(12) United States Patent
Hodage et al.

(10) Patent No.: US 11,771,643 B2
(45) Date of Patent: Oct. 3, 2023

(54) CLEANSING COMPOSITIONS COMPLETELY BASED ON BIO-RENEWABLE SOURCES

(71) Applicant: GALAXY SURFACTANTS LTD., Navi Mumbai (IN)

(72) Inventors: Ananda Shamrao Hodage, Palava (IN); Nirmal Koshti, Piscataway, NJ (US)

(73) Assignee: GALAXY SURFACTANTS LTD., Navi Mumbai (IN)

( * ) Notice: Subject to any disclaimer, the term of this patent is extended or adjusted under 35 U.S.C. 154(b) by 0 days.

(21) Appl. No.: 17/935,651

(22) Filed: Sep. 27, 2022

(65) Prior Publication Data
US 2023/0165784 A1    Jun. 1, 2023

(30) Foreign Application Priority Data
Nov. 30, 2021 (IN) .............................. 202121055405

(51) Int. Cl.
| | | |
|---|---|---|
| *A61K 8/92* | (2006.01) | |
| *A61K 8/49* | (2006.01) | |
| *A61Q 5/02* | (2006.01) | |
| *A61Q 19/10* | (2006.01) | |
| *A61K 8/37* | (2006.01) | |

(52) U.S. Cl.
CPC .............. *A61K 8/922* (2013.01); *A61K 8/375* (2013.01); *A61K 8/4913* (2013.01); *A61Q 5/02* (2013.01); *A61Q 19/10* (2013.01)

(58) Field of Classification Search
CPC ...... A61K 8/922; A61K 8/375; A61K 8/4913; A61Q 5/02; A61Q 19/10
USPC ........................................................ 424/401
See application file for complete search history.

(56) References Cited

U.S. PATENT DOCUMENTS

| | | | | |
|---|---|---|---|---|
| 2011/0223125 A1* | 9/2011 | Hough | ................. | C11D 3/3765 507/224 |
| 2015/0342854 A1* | 12/2015 | Shibuya | .................. | A61P 43/00 424/769 |

FOREIGN PATENT DOCUMENTS

WO    WO-2008043470 A1 *   4/2008   ............... A61K 8/06

* cited by examiner

*Primary Examiner* — Tracy Liu
*Assistant Examiner* — Lucy M Tien
(74) *Attorney, Agent, or Firm* — Fox Rothschild LLP

(57) ABSTRACT

The invention discloses transparent cleansing compositions for personal care which are based on one or more vegetable oils, potassium N-acyl L-prolinate as an anionic surfactant and polyglyceryl-3 oleate as a non-ionic surfactant. The personal care cleansing formulae disclosed herein are totally based on bio-renewable ingredients. Further, in contrast to the compositions from the prior arts, the cleansing compositions of the present invention are free from toxic and petrochemical based ingredients or impurities.

5 Claims, No Drawings

CLEANSING COMPOSITIONS COMPLETELY BASED ON BIO-RENEWABLE SOURCES

CROSS-REFERENCE TO RELATED APPLICATION

This application claims the benefit of priority to Indian Patent Application No. 202121055405 filed Nov. 30, 2021, the disclosure of which is hereby incorporated by reference in its entirety.

FIELD OF INVENTION

The present invention relates to oil based transparent cleansing compositions for personal care. More particularly, the present invention relates to vegetable oil-based cleansing compositions for mild cleansing of skin and hair wherein the compositions are completely based on bio-renewable sources and are devoid of all toxic chemicals present in most of the oil-based cleansing compositions.

BACKGROUND OF THE INVENTION

Oil-based cleansers (30 to 70% oils) are well-suited for the gentle cleansing of the skin and hair, more particularly, for irritated compromised skin. In comparison with aqueous shower gels or body washes, oil-based cleansers lather much less, however, they do a wonderful job of cleansing without removing the lipids of cuticles of hair and the stratum corneum of the skin. In contrast to water-based cleansers, these oil-based cleansers replace the lost lipids and thereby restore the original equilibrium, thus repairing dry skin by reversing it to normal moisturized state. These oil-based compositions moisturize the skin by way of occlusion. Water-based cleansing compositions remove the water-soluble NMF (Natural Moisturizing Factor), whereas it remains undisturbed in the cleansing operation performed by oil-based cleansers. The way water-based cleansing formulae (shampoos and body washes) evolved over time from traditional harsh formulae to 'soap-free' and 'sulphate-free' cleansing systems, the oil-based compositions are evolving too. The traditional oil-soluble 'sulphated' surfactants are also trying to transit to 'sulphate-free' version but without much success. Recently, Unilever launched two 'sulphate-free' shower oils (ApotheCare Essentials and Love Beauty & Planet) which claimed to have 'fast rinsing' feature indicating much less water consumption during cleansing operation.

Oil-based cleansing compositions generally comprises of three major components, namely, 1) oil (e.g., natural vegetable oils), 2) anionic surfactant, and 3) non-ionic surfactant. To this three-component cleansing system, other skin/hair care actives/benefit agents can be added. The examples of these additives, auxiliaries or benefit agents are essential oils or oil-soluble vitamins, ceramides, tea tree oil, and emollients.

Anionic Surfactants in Oil-Based Cleansers

Traditionally, oil-based cleansers have been formulated with oil-soluble surfactant system made up of anionic surfactants and non-ionic surfactants. The most commonly used surfactant system has been MIPA (monoisopropanol amine) laureth sulphate (anionic surfactant) along with fatty alcohol ethoxylates (laureth-3/laureth-4) and fatty alkanol amide (non-ionic surfactant) since this had been the only system available from the surfactant manufacturers (BASF, Zschimmer and Schwarz, Solvay and Sasol) to the personal care formulators (Table 1).

Eventually, skin cleansing products containing irritant MIPA laureth sulphate or TIPA (triisopropanol amine) laureth sulphate (U.S. Pat. No. 6,132,738) have been replaced by TIPA lauroyl sarcosinate in 'sulphate-free, dioxane-free' shower oils launched under the brand of 'Love Beauty & Planet' and 'ApotheCARE Essentials' in the USA.

The substitution of the anionic ether surfactant, MIPA laureth sulphate, by TIPA lauroyl sarcosinate addressed the problem of irritancy for which sulphate-surfactants are known (M. Loden et al., *British Journal of Dermatology*, 150, 1142-1147 (2004)). Use of TIPA-lauroyl sarcosinate, also obviated the exposure of users to carcinogenic 1,4-dioxane the formation of which is unavoidable with current scenario of manufacturing technology of sulphation of fatty alcohol ethoxylate.

However, the anionic surfactants based on primary amine, Mono Isopropanol Amine (MIPA) or a tertiary amine, Tri-Isopropanol Amine (TIPA), still pose a serious problem of generation of highly carcinogenic N-nitrosated amine originating from traces of secondary amine that are present in the MIPA or TIPA which are deployed in the manufacture of surfactants.

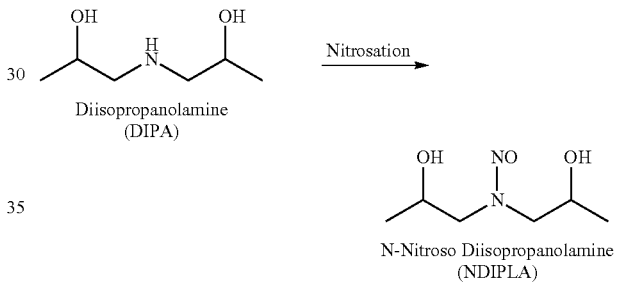

Diisopropanolamine (DIPA)

N-Nitroso Diisopropanolamine (NDIPLA)

The corresponding carcinogenic N-nitroso amine is N-nitrosodiisopropanol amine (NDIPA). The nitroso compounds generated from the secondary amines are highly carcinogenic and hence the permissible limit is 50 ppb (parts per billion) in EU. This necessitates control over the formation of nitroso amines at two stages, namely, 1) during the manufacturing of the amines (primary and tertiary) with strict control on purification (fractionation) to avoid the presence of the secondary amine (diisopropanol amine) as impurity and 2) during the manufacturing of 'finished/final' personal care product ensuring the total elimination of the possibility of nitrosation of secondary amine that might be the impurity in the primary and tertiary amines used. To ensure that the presence of nitrosamine less than 50 ppb in the final personal care product requires not only sophisticated manufacturing set-up but also the analytical capability (chromatography with thermal energy analyzer) which is not a commonly used analytical tool. Furthermore, the possibility of nitrosation during manufacture of personal care product due to various nitrosating agent including oxides of nitrogen in the air can't be ignored. This kind of nitrosation during and after formulation, was the precise reason why personal care products were discovered to contain carcinogenic N-nitroso amines in 1970's and 1980's. (*Food Cosmet. Toxicol.* 15, 423 (1977), *J. Soc. Cosmet. Chemi.* 29, 581-606 (1978)). In view of manufacturing limitation of primary and tertiary amines without the contamination of the secondary amines and also the limitation in having absolute control over accidental nitrosation of the secondary amines, it is advisable to avoid the amines or alkanol amines like MEA (monoethanol amine), MIPA (monoisorpropanol amine) or TEA (triethanol amine), TIPA (triisopropanol amine) in the manufacture of anionic surfactants since none of the commercial manufacturers is offering them with complete absence of secondary amines.

It should be noted that the secondary amines or secondary alkanolamines get converted into highly carcinogenic nitrosamines. The commonly used alkanolamines for oil-based formulations are monoisopropanol amine (MIPA) and tri-isopropanol amine (TIPA) (Table 1 and Table 2). The corresponding nitrosodiethanol amine (NDELA) and nitrosodiisopropanol amine (NDIPLA) and their carcinogenic effect and their occurrence in personal care products have been extensively covered in the literature (*Food Cosmet. Toxicol.* 15, 423 (1977), *J. Soc. Cosmet. Chemi.* 29, 581-606 (1978), *Naturwissenschaften,* 61(7), pp: 328 (1974), *Experimental and Toxicologic Pathology,* 66, 81-88, (2014)).

Nitrosation of the secondary amines or alkanolamines happen with other nitrosating ingredients including oxides of nitrogen in the air. Moreover, 100% pure primary amines or tertiary amines without any secondary amines are not commercially available and these secondary amines that are present in primary and tertiary amine form the carcinogenic N-nitroso compounds. Nitrosamines are easily formed from secondary amines, however, literature also reports their formation from tertiary amines (EMA/369136/2020: Nitrosamines EMEA-H-A5(3)-1490—Assessment report, SCCS/1458/11 (2012), Scientific Committee on Consumer Safety (SCCS): Opinion on Nitrosamines and Secondary Amines in Cosmetic Products, P. A. Smith. et al., *J. Am. Chem. Soc.,* 1967.89(5): p. 1147-1157, Gowenlock, B. et al., *J. Chem. Soc., Perkin Trans.* 2, 1979: p. 1110-1114). The other significant fact about nitrosamines is that once they are formed, they can't be destroyed easily. Their highly toxic nature can be seen in NSRLs (No Significant Risk Level) given in California proposition 65 (0.04 to 0.7 µg/day, Chemicals Considered or Listed Under Proposition 65—OEHHA). For example, N-nitroso-dimethyl amine has NSRL per day of 0.04 µg/day whereas N-nitroso-diethanolamine has NSRL of 0.3 µg/day. Under Cosmetic products regulations (Annex III/entry 60/61/62, updated on February 2021), EC (European Commission) has restricted all amine derivatives. According to ECHA, total nitrosamine content allowed in any personal care products is 50 ppb max. EC also regulates the presence of low molecular weight amines and their salts in personal care products up to 2.5%.

From the above discussion it is very clear that in general aliphatic, low molecular weight amines are to be avoided in personal care, firstly due to their direct toxicity to human and also to the environment when the aqueous washings of amine neutralized surfactant in rinse-off (cleansing) application go back to the nature where the low molecular weight amines can be a serious problem due to their reactivity (highly nucleophilic amino group). Due to extreme corrosive nature on skin, sensitivity to air and temperature that leads to the formation of colored impurities with time, and the volatile nature of low molecular weight amines, handling as well as storage of these raw materials in manufacturing plant are also challenging operations.

The attempt to replace amines in oil-soluble surfactant systems is reported in WO 2017/081698 A1 which teaches replacing amines with basic amino acids (Arginine) to neutralize N-acyl sarcosines. However, the resultant anionic surfactant has poor surfactant properties and surfactant system of WO 2017/081698 A1 also uses petrochemical based ethylene oxide adducts as the non-ionic surfactants.

The Non-Ionic Surfactants in Oil-Based Cleanser Systems

As mentioned above, the amines are used in the manufacture of both anionic and non-ionic surfactants. In case of anionic surfactants, these amines are used in neutralizing the anion portion of surfactants with end group of sulphonic acid or carboxylic acid or partly esterified sulphuric acid. In case of non-ionic surfactants, the amines are condensed with other hydrophobic substances like fatty acids to create the amide link with primary and secondary amines. N-Nitrosation happens with secondary amines. Examples for such non-ionic surfactants with potential for generation of nitrosamines are cocodiethanol amide or cocomonoethanol amide that are used in commercially offered oil-soluble surfactants systems available commercially (Table 1).

TABLE 1

Current oil-soluble surfactant systems offered by surfactant manufacturers:

| Trade name | Ingredients |
| --- | --- |
| Plantapon AF | MIPA Laureth Sulfate (and) Laureth-3 (and) Laureth-7 Citrate |
| Plantapon WW 1000 | MIPA Laureth Sulfate (and) Laureth-4 (and) Cocamide DEA |
| Texapon WW 100 | MIPA Laureth Sulfate (and) Laureth-4 (and) Cocamide DEA |
| Mackadet FBO | MIPA Laureth Sulfate (and) Laureth-3 (and) Cocamide MIPA (and) Butylene Glycol (and) Propylene Glycol |
| MARLINAT 242/90 MC | MIPA Laureth Sulfate (and) Propylene glycol |
| Zetesol TP 300 | TIPA Laureth Sulfate (and) Propylene glycol |
| LUMUROL K 5229 | MIPA Laureth Sulfate (and) Laureth-4 (and) Propylene Glycol |
| Sebumol S 1000 | MIPA Cocoyl sarcosinate and polyglyceryl esters of fatty acid |
| Galsoft TiLS | TIPA Lauroyl sarcosine and Laureth-3 |

It can be seen from Table 1 that almost all commercially available oil-soluble surfactants use lower mole fatty alcohol ethoxylates (laureth-3 and laureth-4) and hence cleanser oils in the market continue to use the same. However, it is relevant to note here that the lower mole ethoxylates of lauryl alcohol are hazardous substances and toxic to marine life (1) Little, A. D. *Human Safety and Environmental Aspects of Major Surfactants*; A Report to The Soap and Detergent Association, New York, 1977.2) Goyer, M. M.; Perwak, J. H.; Sivak, A.; Thayer, P. S.; Little, A. D. *Human Safety and Environmental Aspects of Major Surfactants* (Supplement); A report to: The Soap and Detergent Association, 1981.3) Sivak, A.; Goyer, M.; Perwak, J.; Thayer, P. Environmental and Human Health Aspects of Commercially Important Surfactants. In *Solution Behavior of Surfactants Theoretical and Applied Aspects*; Mittal, K. L.; Fendler, E. J., Eds.; Springer: Boston, 1982; Vol. 1; pp 161-188.4) Talmage, S. S. *Environmental and Human Safety of Major Surfactants: Alcohol Ethoxylates and Alkylphenol Ethoxylates,* 1$^{st}$ Ed.; Lewis Publishers: Boca Raton, 1994.5) Eadsforth, C. V.; Sherren, A. J.; Selby, M. A.; Toy, R.; Eckhoff, W. S.; McAvoy, D. C.; Matthijs, E. Monitoring of environmental fingerprints of alcohol ethoxylates in Europe and Canada. *Ecotoxicol. Environ. Saf* 2006, 64, 14-29.6) Belanger, S. E.; Dorn, P. B.; Toy, R.; Boeije, G. Marshall, S. J.; Wind, T.; Compernolle, R. V.; Zeller, D. Aquatic risk assessment of alcohol ethoxylates in North America and Europe. *Ecotoxicol. Environ. Saf* 2006, 64, 85-99.7) Jurado, E.; Fernández-Serrano, M.; Núñez-Olea, J.; Luzón. G.;

Lechuga, M. Acute toxicity and relationship between metabolites and ecotoxicity during the biodegradation process of non-ionic surfactants: fatty-alcohol ethoxylates, nonylphenol polyethoxylate and alkyl polyglucosides. *Water Sci. Technol.* 2009, 59, 2351-2358.8) Sanderson, H.; Compernolle, R. V.; Dyer, S. D.; Price, B. B.; Nielsen, A. M.; Selby, M.; Ferrer, D.; Stanton, K. Occurrence and risk screening of alcohol ethoxylate surfactants in three U.S. river sediments associated with wastewater treatment plants. *Sci. Total Environ.* 2013, 463-464, 600-610).

US20200289401A1 teaches a way around irritating 'sulphate surfactants' and 'marine pollutants' lower mole fatty alcohol ethoxylates. The prior art teaches to replace lauryl alcohol ethoxylates by lauryl alcohol, however, the strong and unpleasant odor of lauryl alcohol is almost impossible to mask with fragrance in the cleanser formulation. The unpleasant odor of fatty alcohol lingers on the skin for a long time. The reason for this long-lasting malodor is probably due to easy fusion of fatty alcohol molecules with the lipids of stratum corneum.

Thus, the serious limitations of the oil-based cleansing products in the market are that the ingredients employed in surfactant systems have toxicity to both, human being as well as environment. For example, the non-ionic fatty alcohol ethoxylate are marine pollutants.

The biggest concern is the extent of environmental damage that the amines/alkanol amines would be doing when they go back to the nature after the usage as cleansing products. The alkanol amines that are being used are reactive organic molecules with terminal amino and hydroxyl functionalities which are capable of reacting with many substrates in the environment. The formation of carcinogenic nitrosamines is an additional concern. Fatty alcohol ether sulphates are also under the radar because traces of carcinogenic of 1,4-dioxane content. Recently, state government of New York passed bill enforcing strict control over carcinogenic 1,4-dioxane (State bill NY 54389B of New York state, USA, 2020).

Additionally, according to a recent (October 2021) market research done by Mintel (www.mintel.com), over 600 oil-based cleansers have been launched in last five years. It is very clear that most of these oil-based cleansers seem to be using MIPA laureth sulphate (83016-76-6) or TIPA laureth sulphate (66161-06-2) as anionic surfactants, and fatty alcohol ethoxylate and alkanol amide as non-ionic surfactants. Out of the two ethoxylated sulphate surfactants, MIPA laureth sulphate seems to be predominant with 596 launches whereas 61 products have been launched with TIPA laureth sulphate. MIPA laureth sulphate based products had been introduced in 1980's and 90's (US 437154845 (1983), U.S. Pat. No. 4,488,564 (1984), 5,653,988 (1997), 6,132,738 (2000), DE 197 42 480 (2008)). TIPA laureth sulphate based products seemed to have been introduced subsequently. As mentioned in Table 1, the surfactant system offered by the major surfactant manufacturers is made up of amine neutralized ether sulphated surfactants, alcohol ethoxylates and fatty alkanolamides. From the recent launches in 2021 one can see that (Table 2) MIPA laureth sulphate and laureth-4 are the surfactants used by the industry since these are offered by the surfactant industry despite the problems associated with amines, ether sulphate chemistry and fatty alcohol ethoxylate. Amine neutralized fatty alcohol ether sulphates are the source of carcinogenic 1,4-dioxane and nitrosamine.

TABLE 2

Surfactant systems of recently launched oil-based cleansing products

| Company/country | Launch date | Surfactant system |
| --- | --- | --- |
| Beiersdorf/Croatia | October 2021 | MIPA laureth sulphate, laureth-4 |
| Fur/USA | September 2021 | MIPA laureth sulphate, laureth-3 |
| AcoHUD Nordic/Denmark | September 2021 | MIPA laureth sulphate, laureth-4 |
| Rituals Cosmetics/Portugal | September 2021 | MIPA laureth sulphate, laureth-2 |
| Beiersdorf/South Africa/Slovakia | September 2021/ August 2021 | MIPA laureth sulphate, laureth-4 |
| Lidl/Germany | August 2021 | MIPA laureth sulphate, laureth-4, DEA Cocamide |
| Lyko Group/Sweden | July 2021 | MIPA laureth sulphate, laureth-4 |
| Laboratorio Farmaervas/Brazil | May 2021 | MIPA laureth sulphate, laureth-4 |
| Body Shop/Belgium | May 2021 | MIPA laureth sulphate, laureth-4 |
| L'Occitane/Sweden | February 2021 | TIPA laureth sulphate, laureth-3 |
| FIT/Germany | March 2021 | TIPA laureth sulphate, laureth-2 |
| Qi Ran Bio-Technology/China | July 2021 | TIPA laureth sulphate, laureth-3 |

Fatty alkanolamides are the source of carcinogenic nitrosamines due to monoethanol amine or diethanol amine that are used in manufacturing of fatty alkanol amides (cocoamide MEA; 68140-00-1, cocoamide DEA; 68603-42-9). The other non-ionic surfactants used by the major suppliers (Table 1) is fatty alcohol ethoxylate with lower moles of ethylene oxides (2, 3, or 4 EO, 3055-93-4; 68002-97-1; 68439-50-9) that are toxic to marine life.

U.S. Pat. No. 8,383,090 (2013) addresses the toxicity issue of 1,4-dioxane partially by replacing ether sulphate with amine neutralized N-acyl sarcosinate in the oil-soluble surfactant systems. However, amines used in these anionic surfactants are still source of carcinogenic nitrosamines.

U.S. Pat. No. 9,320,697 (2016) replaces ether sulphate surfactants with petrochemical based dioctyl sulphosuccinate as anionic surfactant but the system reported in this patent uses fatty alkanol amides that are the source of carcinogenic nitrosamines (N-nitrosodiethanol amine was reported in cosmetic products where fatty alkanol amides were used. *Food Cosmet. Toxicol.* 15, 423 (1977), *J. Soc. Cosmet. Chemi.* 29, 581-606 (1978)).

Thus, none of the surfactant systems hitherto reported for oil-based cleansers is 1) totally free from ingredients that are reported to be toxic to environment, human, and other living organisms and 2) is totally derived from bio-renewable feedstocks.

Hence, there is a need to create oil-based stable cleansing compositions to deliver the benefits of vegetable oils and other oil-soluble actives with a surfactant system that would be devoid of 1) amines 2) alkyl ether sulphate-surfactant, and 3) lower mole ethoxylates thereof. In view of ecotoxicity, there is a need for an eco-safe composition that would be completely made from bio-renewable materials. While achieving this, there is a challenge to create the surfactant system having these oil-based mild cleansers cosmetically (organoleptically) acceptable and thermodynamically stable (color stability and no phase separation during freeze thaw cycles or color deterioration over time).

The inventors of the present invention surprisingly found novel cleansing compositions those are completely based on bio-renewable ingredients and address all ecotoxicity, carcinogenicity and stability related issues mentioned in the prior arts.

Inventors of the present invention surprisingly found totally non-toxic (to both human and ecosystem) and totally green (derived from bio-renewable source) oil-based cleansing composition. These totally green cleansers are created with potassium N-acyl L-prolinate as anionic surfactant (potassium N-lauroyl L-prolinate, CAS 168214-73-1, potassium N-cocoyl L-prolinate) in combination with 'green' non-ionic surfactant namely, polyglyceryl-3 oleate (CAS 33940-98-6) and one or more vegetable oil/s.

Objectives of the Invention

The main objective of the present invention is to provide practically colorless transparent vegetable oil-based cleansers completely derived from bio-renewable ingredients. The objective is to create oil-based cleansers with minimum 99% of 'natural origin' content as per the definition of ISO 16128-2.

Another objective of the present invention is to create oil-based cleansers using ingredients that are nontoxic and without any carcinogenic impurities even at trace level. In other words, the objective is to avoid amine based anionic surfactants and ethylene oxide based non-ionic surfactants, without compromising the performance.

Yet another objective of the present invention is to create oil-based cleansers with robust stability to withstand the extreme changes in climate that are experienced in different geographies during the life cycle of the product. The oil-based cleansers meant for personal care application are stable at of $-20°$ C. as well as at $45°$ C.

SUMMARY OF THE INVENTION

The present invention provides stable, colorless to light colored, transparent vegetable oil-based cleansers for personal care made from the bio-renewable and biodegradable ingredients. The compositions of the present inventions are free from ingredients that are ecotoxic and are free from ingredients that contain carcinogens like 1,4-dioxane or nitrosamines.

Oil-based cleansing compositions of present invention comprise of three major components, namely, 1) oil (natural vegetable oils, synthetically derived triglycerides from vegetable oil source), 2) anionic surfactant, and 3) non-ionic surfactant. To this three-component cleansing system, other skin/hair care actives/benefit agents can be added. These additives, auxiliaries or benefit agents can be essential oils or oil-soluble vitamins, ceramides, tea tree oil, and emollients etc.

More particularly, the transparent vegetable oil-based cleansing compositions for personal care comprise of A) potassium N-acyl L-prolinate (Formula I), where acyl group is either lauroyl or cocoyl, B) polyglyceryl-3 oleate (Formula II), C) one or more vegetable oils, D) optionally, emollients, skin actives and hair actives and E) water content ranging from 0.0 to 3.0% by weight of the total composition. The ratio of potassium N-acyl L-prolinate:polyglyceryl-3 oleate:one or more vegetable oils: 1.5:2.0 to 4.5:3.0 to 7.5 by weight. The said compositions are stable towards the extreme variations in cold ($-20°$ C.) and hot temperatures as established by freeze-thaw cycles and stability at $45°$ C. These oil-based cleansers are useful for cleansing of dry skin in the winter as well as for cleansing of compromised skin.

Formula I

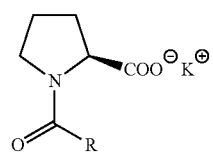

Formula II

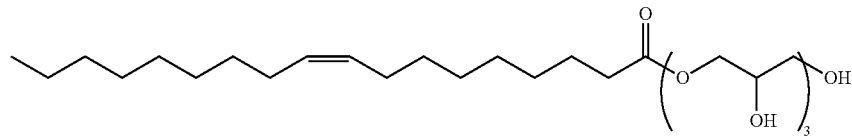

In some embodiments, cleansing composition comprises N-acyl L-prolinate of Formula I selected from either N-cocoyl L-prolinate or N-lauroyl L-prolinate or substantially a mixture of both. More specifically, N-acyl L-prolinate of Formula I is N-cocoyl L-prolinate and N-acyl L-prolinate of Formula I is N-lauroyl L-prolinate.

In some embodiments, vegetable oil is selected from but not limited to safflower oil, soybean oil, sunflower oil, coconut oil, palm kernel oil, olive oil, jojoba oil, neem oil, macadamia oil, argan oil, almond oil, avocado oil, grapeseed oil, soap nut oil, meadowfoam seed oil, wheat germ oil, rice bran oil, rosemary oil, castor oil, rapeseed oil, tung oil, mustard oil, peanut oil, shea butter an mixtures thereof. Preferably, vegetable oils are selected from safflower oil, sunflower oil, soybean oil, castor oil and olive oil or mixture thereof.

In some embodiments, cleansing composition comprises from about 0% to about 3.0% of water by weight of said cleansing composition.

The invention will be now described in detail and in the manner it is performed.

DETAILED DISCUSSION

It is evident from the background that the oil-based cleansing composition available in the market are based on either laureth based anionic surfactants or amine neutralized anionic surfactants, both of which lead to incorporation of carcinogenic impurities (like 1,4 dioxane and nitrosamine) as well as environmental toxicity. Few formulations that are devoid of these carcinogenic impurities were developed but exhibit poor performance in terms of foaming and stability.

Inventors of the present invention surprisingly found totally non-toxic (to both human and ecosystem) and completely green (derived from bio-renewable source) an oil-based cleansing composition. These oil-based green cleansing formulations are created with potassium N-acyl L-prolinate as anionic surfactant (potassium N-lauroyl L-prolinate, CAS 168214-73-1, potassium N-cocoyl L-prolinate) in combination with 'green' non-ionic surfactant polyglyceryl-3 oleate (CAS 33940-98-6) and one or more vegetable oil.

The present invention relates to the transparent vegetable oil-based cleansing compositions for personal care comprise of A) potassium N-acyl L-prolinate (Formula I), where acyl group is either lauroyl or cocoyl, B) polyglyceryl-3 oleate (Formula II), C) one or more vegetable oils, D) optionally, emollients, skin actives and hair actives and E) water content ranging from 0.0 to 3.0% by weight of the total composition. The ratio of potassium N-acyl L-prolinate:polyglyceryl-3 oleate:) one or more vegetable oils: 1.5:2.0 to 4.5:3.0 to 7.5 by weight. The said compositions are stable towards the extreme variations in cold (−20° C.) and hot temperatures as established by freeze-thaw cycles and stability at 45° C. These oil-based cleansers are useful for cleansing of dry skin in the winter as well as for cleansing of compromised skin.

highly biocompatible, non-essential amino acid well known for its skin and hair conditioning applications as well as animal nutrition.

The use of N-acyl L-prolinates as surfactants in personal care has been reported by Comini et al. (EP 2276453) wherein the anionic surfactants are used for solubilizing essential oils (basil oil, *eucalyptus* oil and sage oil) in aqueous formulations. The goal of EP 2276453 is to substitute traditional ethylene oxide based non-ionic surfactants such as PEG 40 hydrogenated castor oil, PPG 26, and trideceth-9 with N-acyl prolinates for solubilizing a small quantity of essential oils in aqueous formulation.

N-Acyl L-prolinates are prepared as per the details given in the experimental section. Both, sodium and potassium salts of cocoyl and lauroyl prolinates are synthesized using corresponding acyl chloride and L-Proline under Schotten Baumann conditions. Syntheses of acyl prolinates and NMR data are described in detail.

The vegetable oil-based cleansers of the present invention are made by mixing the two out of the three ingredients (potassium N-acyl L-prolinate and polyglyceryl-3 oleate) together at room temperature to get a homogeneous mass. To this, vegetable oil is added under stirring to get the homogeneous transparent mass. To this, other skin or hair care actives, benefit agents and other adjuvants are added. All compositions (except comparative examples 1B to 1E) described in Examples 1 to 17 employ either potassium N-cocoyl L-prolinate or potassium N-lauroyl L-prolinate. Both, N-cocoyl and N-lauroyl potassium salts of L-proline afford very stable compositions in contrast with corresponding sodium salts. For example, a composition made by simple mixing of ingredients (safflower oil, potassium N-lauroyl L-prolinate and polyglyceryl-3 oleate) at room temperature as shown in Example 1 results in a very stable

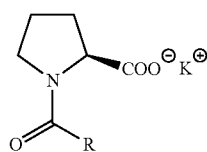

Formula I

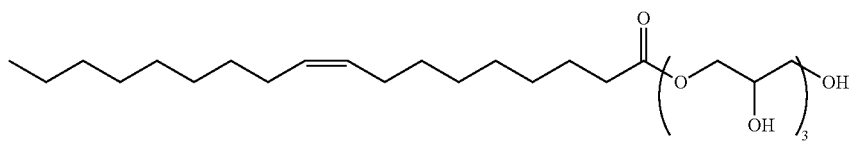

Formula II

Unexpectedly, oil-based cleansers using combination of potassium N-acyl L-prolinate, polyglyceryl-3 oleate and vegetable oils, are found to be extremely stable towards the freeze-thaw cycles performed at −20° C. and 25° C. for 24 h as well as at higher temperatures in the zone of 40-45° C. Another unexpected finding is that the foaming performance of these compositions is found to be significantly superior when compared with the foaming performance of the compositions made with amine neutralized sarcosinate surfactant (TIPA-lauroyl sarcosinate) in place of potassium N-acyl L-prolinates.

Amine-Free Anionic Surfactants for Oil-Based Compositions: Potassium N-Acyl L-Prolinates L-Proline is being manufactured on commercial scale via bacterial fermentation process (e.g. Starlake Bioscience Co. Inc., CHINA; Maycos Italiana S. R. L., ITALY; Kyowa Hakko Bio Singapore Pvt. Ltd., SINGAPORE; etc.). It is and transparent composition. However, the same composition with only change in composition effected by replacing potassium salt with sodium N-lauroyl L-prolinate (comparative Example 1A) doesn't give a transparent homogeneous solution even at room temperature.

It is also relevant to note here that neither sodium nor potassium salt of acyl sarcosine provides a stable and homogeneous composition (comparative Example 1B & 1C) at room temperature and there is no question of testing the stability by Freeze-Thaw cycles.

Current literature reports MIPA/TIPA neutralized acyl sarcosines as anionic surfactant of choice for oil-based formulation (U.S. Pat. No. 8,383,090B2 and US20200289401A1), last entry in Table 1). Amine neutralized acyl sarcosinates provide homogeneous transparent formulations that are stable towards 'freeze-thaw' cycles, however, these compositions containing 10 to 30% by weight of MIPA or TIPA neutralized acyl sarcosinates deteriorate in color. The color of freshly made compositions is pale yellow, however, it becomes brown (5.0 to 8.0 Gardner) at room temperature in few months. Extremely rapid color deterioration is observed at 45° C. over a short period of time. The freshly made pale yellow colored oil-based cleanser turns dark brown raising the concern about the extremely limited shelf life (comparative example 1D) because of loss of aesthetics due to temperature variations in product's life cycle. The compositions of comparative examples using amine neutralized anionic surfactants (comparative example 1D) does also suffer from serious inferior performance of foaming (260 mL) compared to Example 1 which uses potassium N-lauroyl L-prolinate when measured using Hart DeGeorge blender method (Hart, J. R., et. al. *J. Soc. Cosmet. Chem.* 31:223 (1980)). Thus, although N-Acyl sarcosinates are known for their high foaming power in water-based formulations, oil-based surfactant system of the present invention containing N-acyl prolinates gives much higher lather compared to TIPA-lauroyl sarcosinate (foam volume in "Example 1 and Example 1D" or "Example 1E and Example 17").

Also, the amine neutralized sarcosinate does not form a stable composition when % of vegetable oil is significantly higher (75%, comparative Example 1E) whereas the surfactant system of the present invention (potassium N-acyl L-prolinate and polyglyceryl-3 oleate) results in a stable composition with higher % (75%) of vegetable oil (Example 17).

Thus, it can be seen that typical % of anionic surfactant is in the range of 10 to 30% by weight of the total composition as exemplified in compositions (Examples 1 to 16) wherein the non-ionic surfactant polyglyceryl-3 oleate is common. These compositions use a variety of vegetable oils, delivering a variety of personal care benefits. The ratio of potassium N-acyl L-prolinate to polyglyceryl-3 oleate is 1.5:2.0 to 4.5 (Example 1 to 16). While the ratio by weight of three component to each other is; potassium N-acyl L-prolinate: polyglyceryl-3 oleate:vegetable oil: 1.5:2.0 to 4.5:3.0 to 7.5.

Vegetable Oils:

Vegetable oil is a significant component of the compositions of the present invention. Vegetable oils can be used from 30 to 70% by weight relative to the composition.

Vegetable Oils for the compositions of the present invention are selected from sunflower seed oil, safflower oil, olive oil, soyabean seed oil, avocado oil, coconut, jojoba, neem oil, lavender, argan oil, macadamia oil, almond oil, grapeseed oil, meadowfoam seed oil, wheat germ oil, rice bran oil, rosemary oil, castor oil, rapeseed oil, tung oil, mustard oil, peanut oil, and shea butter. All vegetable oils have benefits associated either for skin or for hair or in many cases for both skin and hair. In case of some oils the benefits go beyond moisturizing, nourishing, repairing, anti-inflammatory, soothing and sensory. Vegetable oils like neem oil or tea tree oil are deployed for their antimicrobial activity or tung seed oil for its film forming property. Rosemary oil is known for collagen boosting and gets used in skin tightening application. Mustard seed oil is used for anti-inflammatory effect on scalp. Examples 1 to 17 of the specification show a variety of oils used for cleansing compositions, though most commonly used vegetable oils are safflower, castor oil, soyabean oil and sunflower oil. In addition, olive oil (Example 5, 7), avocado oil (Example 8), neem, jojoba (Example 10), almond oil (Example 11), tung oil (Example 12), argan oil and coconut oil (Example 13) have been used for various benefits. Compositions of Examples 13 and 14 are for hair care and are based on coconut oil and other hair benefit agents.

Polyglyceryl-3 Oleate

Polyglyceryl-3 oleate is the non-ionic surfactant (CAS No 3394-98-6). This green surfactant is produced from glycerin and oleic acid, essentially both bio-renewable sources. It is used from 15% to 50% by weight relative to the cleansing composition. In combination with potassium N-acyl L-prolinates, it gives exceptionally stable compositions in wide weight by weight ratio (Example 15 and 16).

Skin and Hair Benefit Agents:

The skin benefit agents for the compositions of the present invention can be selected from all oil soluble skin care agents. The preferred skin care ingredients are derived from bio-renewable sources. The examples of these are oil-soluble UV-absorbers, skin lightening agents, anti-acne agents, fatty acid or fatty alcohol derived esters-emollients, derma purifiers (Example 7, capryoloyl glycine, CAS 14246-53-8 and undecylenoyl glycine, CAS 54301-26-7), vitamins (Example 8), ceramides (Example 9), lipopeptides (lipid conjugated oligo peptides), and essential oils. Oil soluble derivatives are easy to incorporate however, the composition of the present invention can accommodate adequate level of water-soluble actives like water-soluble vitamins like niacinamide, ascorbic acid or panthenol. Niacinamide (Example 5) as skin lightening agent or ceramide (to restore barrier function in dry skin) can be delivered to skin via oil-based cleansers of the present invention.

In another embodiment, the actives for hair care compositions of the present invention can be selected from arginine, panthenol, undecylenoyl glycine (anti-yeast, Example 7). Other actives like derma purifier like capryloyl glycine (Example 6, 7) or cinnamon oil (natural UV-absorber, Example 6), alpha eleostearic acid (UV absorber, film former, Example 6) or its derivatives can be deposited via vegetable oil-based cleansers. Thus, hair care or skin care actives of natural origin or nature derived can be part of the compositions of present invention.

In yet another embodiment, compositions of the present invention can also be potentially used as medicated shower oils for pet. Some of the essential oils that are reported to be anti-tick or anti-lice or anti-flea by being insect repellant by their strong aroma due to which the critters can't perceive the body odors of pets (lavender oil, tea tree oil, rosemary oil, clove oil, basil oil, thyme oil, lemongrass oil, neem oil, citronella oil, cedar oil) can be accommodated in compositions of present invention to create medicated shower oil for pet care (Example 12). Emollients can be selected from glyceryl mono laurate (Example 1, CAS 27215-38-9), lauryl lactylate (Example 2, CAS 910661-93-7), lauryl lactate (Example 3, CAS 6283-92-7), lauryl citrate (Example 4, CAS 65277-53-4) and coco glycerides (Example 8, CAS 92045-31-3), Shae butter (Example 8, CAS 91080-23-8), caprylic capric triglyceride (Example 10, CAS 65381-09-1) or any other ester types that are typically made from bio-renewable sources.

The constituents of three component system and general methodology to make oil-based compositions and their stability are reported in seventeen examples shown in examples 1-17. The technical advancement over the prior arts is summarized below.

Advantages

1) The biggest advantage of the compositions of the present invention is that it avoids all earlier used ingredients that are either toxic or they contain highly toxic impurities. For example, MIPA (monoisopropanol amine) or TIPA (triisopropanol amine) based fatty alcohol ether sulphates have both carcinogens, namely, 1,4-dioxane and nitrosoisopropanol amine. Also, earlier used non-ionic surfactants fatty alcohol ethoxylates are marine pollutant.

2) The second biggest advantage is that compositions of the present invention are completely made from bio-renewable raw materials. The carbon content of these compositions is 100% bio-renewable. All the feedstocks are either bio-synthesized or bio-derived. The feed stocks for the surfactant systems of the present invention are vegetable fatty acids, L-Proline, glycerin, and lactic acid which are all derived from bio-renewable source. Thus, natural origin content of the compositions of the present invention is 100% as per of ISO 16128-2 (2017).

3) All ingredients used in the compositions of the present invention are biodegradable and inherently free from any toxic degraded product.

4) The compositions of the present invention are very stable towards extremes of temperature and extended time compared to amine based anionic surfactants. These compositions are stable towards freeze-thaw cycles performed at −20° C. for 24 h and at 25° C. for 24 h as a part of freeze and thaw cycle. The compositions of the present invention are also stable at 45° C. for a long period of month with respect to phase separation as well as color deterioration. This is the big advantage over current MIPA or TIPA based oil-cleansers for personal care. Oil-based cleansers are designed to alleviate the 'dry' conditions (xerosis cutis) caused by the cold weather. Oil based cleansers (shower oils) are needed by the seniors since the chronological aging results in dry skin condition and cold weather makes it worst. Hence shower oils have their own importance during the winter season. It is absolutely necessary that the oil-based cleansers possess good thermodynamic stability to withstand vagaries of nature. Robust stability towards cold temperature helps in all aspects of commercial activities such as transportation, storage and longer shelf-life of the final offerings for consumers. Thus, the problem of infinite thermodynamic stability is fully addressed by the freeze-thaw stable compositions of the present invention. The vegetable oil-based cleansing compositions of the present invention meet the stability requirement without compromising on the performance, % of natural origin content or the eco-friendliness/sustainability. The shower oil compositions disclosed in this invention are stable towards extreme variations of the temperatures ranging from 45° C. to freezing temperatures of −20° C..

EXPERIMENTAL

The present invention is now described by way of working non-limiting illustrative examples. These examples are provided for illustrative purposes only and are not intended to limit the scope of the invention as defined in the claims below.

L-Proline, L-Arginine, Vitamin E, DL-Panthenol, Niacinamide and Ascorbic acid (Vitamin C) are procured from local manufacturers (like Sisco Research Laboratories Pvt. Ltd. INDIA, Matrix Life Science Pvt Ltd. INDIA, N. S. Chemicals, INDIA, Western Drugs Ltd. INDIA, and Advance In Organics, INDIA, respectively). Caprylic capric triglyceride, capryloyl glycine and undecylenoyl glycine are used from in-house (Galaxy Surfactants Ltd.) commercial production. Polyglyceryl-3 Oleate and glyceryl laurate are purchased from Fine Organics Ltd, INDIA. Ceraminde-3 and Cocoglyceride (Myritol® 331) are procured from Doosan Corporation, South Korea and BASF, USA, respectively.

Lauryl lactate, lauryl lactylate, and lauryl citrate are synthesized in lab using reported methods in literature (*Journal of Surfactants and Detergents* (2016), 19(2), 343-351, and WO 2003075880).

Sunflower seed oil, safflower oil, olive oil, avocado oil, jojoba, argan oil, almond oil, castor oil, and shea butter are imported from TRI-K Industries, Inc. USA. Tung oil is imported from Guangxi Sinotung Trading Co. Ltd, CHINA. Neem oil, citronella oil, cedarwood oil and lavender oil (from Rmayra Naturals Impex, INDIA), soyabean seed oil, coconut oil and palm kernel oil (from AAK Kamani Pvt. Ltd., INDIA), and rapeseed oil (from Vaishnodevi Refoils & Solvex, INDIA) all are procured from local suppliers.

The present invention is now described by way of working on limiting illustrative examples. These examples are provided for illustrative purposes only and are not intended to limit the scope of the invention as defined in the claims below.

Synthesis of N-Lauroyl L-Proline

N-Lauroyl L-Proline is synthesized in two steps. In the first step, sodium N-lauroyl L-prolinate is made by the Schotten-Baumann chemistry reported in the literature (EP 3100715A1; U.S. Pat. No. 9,456,971 B2; U.S. Pat. No. 9,782,336 B2; U.S. Pat. No. 9,187,407B2).

To a stirred mixture of L-proline (126.5 g, 1.1 moles, 1.05 eq.) solution in water (800 mL) at 20-25° C. under nitrogen, lauroyl chloride (228.5 g, 1.05 moles, 1.0 eq.) and 48% aqueous solution of sodium hydroxide (184 g, 2.16 moles, 2.05 eq.) are added simultaneously over the period of 3 hrs. while maintaining pH of the reaction mass in the range of 10.5-11.5. The reaction mixture is further stirred for one hour at the same temperature. Sodium N-lauroyl L-prolinate, thus formed, is a clear liquid: quantity: 1334 g; solids content: 30.12%; NaCl: 4.59%.

The clear aqueous solution of sodium N-lauroyl L-prolinate (1334 g) thus obtained is acidified with hydrochloric acid solution (112 g, 1.0779 moles) in the second step at room temperature and the pH of the reaction mass is adjusted in the range of 1.0-1.5. The aqueous layer is then removed and upper organic layer of N-lauroyl proline is washed (100 mL) of fresh water to remove traces of mineral acidity in the organic layer. The washed organic phase is further dried using rotary evaporation at room temperature under vacuum to afford acyl proline as low viscous pale yellow colored liquid (yield: 301 g, 95%; acid value: 186 mg of KOH/g; moisture content: 0.35%).

IR (neat): 2750-3100 $cm^{-1}$ (carboxylic acid O—H stretch); 2853 $cm^{-1}$ & 2923 $cm^{-1}$ (C—H stretch); 1736 $cm^{-1}$ (>C=O stretch from —COOH); 1650 $cm^{-1}$ (>C=O stretch from —CON<amide); 1455 $cm^{-1}$ (C—H bend from alkyl chain). $^1H$ NMR (400 MHz, $CDCl_3$): δ 0.88 (t, J=6.8 Hz, 3H), 1.26-1.32 (m, 16H), 1.63-1.69 (m, 2H), 1.99-2.06 (m, 3H), 2.36 (t, J=7.2 Hz, 2H), 2.43 (br, 1H), 3.47-3.49 (m, 1H), 3.57-3.61 (m, 1H), 4.61 (t, J=5.2 Hz, 1H), 7.73 (br, 1H). $^{13}C\{^1H\}$ NMR (400 MHz, $CDCl_3$): δ 13.97 (—$CH_3$), 22.54, 24.39, 24.62, 27.34, 29.18, 29.24, 29.32, 29.46, 31.76, 34.34, 47.70, 59.73, 172.50 (—CO—N<), 175.24 (—COOH).

Synthesis of Potassium N-Lauroyl L-Prolinate

To the dispersion of N-lauroyl L-proline (100 g, 0.3367 moles) in 144 g of water, 50% aqueous solution of potassium hydroxide (40 g, 0.3500 moles) is added dropwise at room temperature and pH is adjusted to 7.0. The aqueous solution of potassium N-lauroyl L-prolinate thus formed is dried on rotary evaporation under vacuum to afford pure potassium N-lauroyl L-prolinate as highly viscous pale yellow colored liquid (yield: 112 g, 99.2%; moisture content: 0.58%).

Synthesis of N-Cocoyl L-Proline

The N-cocoyl L-proline is prepared in analogous way as depicted for N-lauroyl L-proline. To a solution of L-proline (83 g, 0.72 moles, 1.05 eq.) in water (520 mL) at 20-25° C., cocoyl chloride (150 g, 0.69 moles, 1.0 eq.) and sodium hydroxide solution (48% aq. sol., 120 g, 1.44 moles, 2.09 eq.) are added simultaneously over the period of 3 hrs. while maintaining the reaction pH in the range of 10.5-11.5. The reaction mixture is further stirred for 2 hrs. at room temperature. Sodium N-cocoyl L-prolinate, thus formed, is clear liquid (870 g); solids content: 30.40%; NaCl: 4.64%.

This clear solution of sodium N-cocoyl L-prolinate (870 g, 0.70 moles, 1 eq.) is then acidified with hydrochloric acid solution (74 g, 0.7095 moles, 1.01 eq.) at room temperature and the pH of the reaction mass is adjusted in the range of 1.0-1.5. The aqueous layer is then removed and upper organic layer of N-cocoyl proline is washed (60 mL) of fresh water to remove traces of mineral acidity in the organic layer. The washed organic phase if further dried using rotary evaporation at room temperature under vacuum to afford acyl proline as low viscous pale yellow colored liquid (yield: 200 g, 95.7%; acid value: 184 mg of KOH/g; moisture content: 0.42%).

Synthesis of Potassium N-Cocoyl L-Prolinate

Potassium N-cocoyl L-prolinate is prepared in analogous way as depicted for potassium N-lauroyl L-prolinate. To the dispersion of N-cocoyl L-proline (120 g, 0.40 moles) in 174 g of water, 50% aqueous solution of potassium hydroxide (46 g, 0.4099 moles) is added dropwise at room temperature and pH is adjusted to 7.0. The aqueous solution of potassium N-cocoyl L-prolinate thus formed is dried on rotary evaporation under vacuum to afford pure potassium N-cocoyl L-prolinate as highly viscous pale yellow colored liquid (yield: 134 g, 98.9%; moisture content: 0.74%).

General Procedure for the Preparation of Oil-Based Cleansing Formulations (Examples 1-12)

Phase A: The mixture of polyglyceryl-3-oleate and potassium N-lauroyl L-prolinate is stirred thoroughly at room temperature till the mixture becomes homogeneous.

Phase B: Oil-soluble actives (emollient, vitamins, derma purifiers, fragrances, antioxidants, antiaging active, anti-acne active, other oil-soluble actives etc.) are added to vegetable oil or mixtures of vegetable oils and stirred at room temperature till a homogeneous transparent solution is formed.

Preparation of oil-based cleanser: Phase A and phase B are mixed together at room temperature to form one transparent homogeneous composition.

General Procedure for Freeze-Thaw Stability Study

The oil-based cleanser composition thus prepared is kept at to −20° C. for 24 h and then allowed to thaw back to 25° C. and kept at the same temperature for 24 h. The procedure is repeated for two more times (total three cycles) and finally sample is kept at room temperature for 12 days. At the end of $12^{th}$ day, it is examined for any physical and visible change like separation of phases, crystallization or precipitation etc.

General Procedure for High Temperature Stability

It is measured by keeping samples of oil-based cleansers (examples 1-12) at 45° C. for a month in a temperature controlled oven. During the course of stability, the samples are examined for any visible changes and at the end of $30^{th}$ day, the samples are examined for the change in the chemical composition.

Hart DeGeorge Blender Method: General Procedure (Hart, J. R., Et. Al. *J. Soc. Cosmet. Chem.* 31:223 (1980))

Oil-based formulae of Example 1 to 12 (5 g) is dispersed in hard water (95 mL, hardness 150 ppm) and the whole dispersion (100 mL) is transferred to a kitchen blender. It is mixed at a speed of 20,000 rpm for 60 sec. Foam generated is measured by transferring it to a suitable measuring cylinder.

Example 1

Cleansing Oil Composition Using Potassium N-Lauroyl L-Prolinate and Safflower Oil

| Ingredients | % (w/w) |
| --- | --- |
| Safflower Oil (*Carthamus tinctorius*) | 50 |
| Polyglyceryl-3 Oleate | 30 |
| Glyceryl Laurate | 5 |
| Potassium N-Lauroyl L-Prolinate | 12 |
| Water | 3 |
| Total | 100 |

| Evaluation Parameter | Remark |
| --- | --- |
| Three cycles Freeze (−20° C., 24 h) Thaw (25° C., 24 h) | Passes |
| Stability at 45° C., over one month | Stable, Transparent Color: 220 APHA (Initial color: 105 APHA) |
| Foam (5% in water. Hart DeGeorge) | 450 mL |

Example 1A: Comparative Example

Cleansing Oil Composition Using Sodium N-Lauroyl L-Prolinate and Safflower Oil

| Ingredients | % (w/w) |
| --- | --- |
| Safflower Oil (*Carthamus tinctorius*) | 50 |
| Polyglyceryl-3 Oleate | 30 |
| Glyceryl Laurate | 5 |

| Ingredients | % (w/w) |
|---|---|
| Sodium N-Lauroyl L-Prolinate | 12 |
| Water | 3 |
| Total | 100 |

| Evaluation Parameter | Remark |
|---|---|
| Three cycles Freeze (−20° C., 24 h) Thaw (25° C., 24 h) | Fails. Its unstable, even at RT |
| Stability at 45° C., over one month | Unstable, separates into two layers |
| Foam (5% in water. Hart DeGeorge) | 520 mL |

Example 1B: Comparative Example

Cleansing Oil Composition Using Sodium N-Lauroyl Sarcosinate and Safflower Oil

| Ingredients | % (w/w) |
|---|---|
| Safflower Oil (*Carthamus tinctorius*) | 50 |
| Polyglyceryl-3 Oleate | 30 |
| Glyceryl Laurate | 5 |
| Sodium N-Lauroyl Sarcosinate | 12 |
| Water | 3 |
| Total | 100 |

| Evaluation Parameter | Remark |
|---|---|
| Three cycles Freeze (−20° C., 24 h) Thaw (25° C., 24 h) | Fails. Its unstable, even at RT |
| Stability at 45° C., over one month | Unstable, separates into two layers |
| Foam (5% in water. Hart DeGeorge) | 650 mL |

Example 1C: Comparative Example

Cleansing Oil Composition Using Potassium N-Lauroyl Sarcosinate and Safflower Oil

| Ingredients | % (w/w) |
|---|---|
| Safflower Oil (*Carthamus tinctorius*) | 50 |
| Polyglyceryl-3 Oleate | 30 |
| Glyceryl Laurate | 5 |
| Potassium N-Lauroyl Sarcosinate | 12 |
| Water | 3 |
| Total | 100 |

| Evaluation Parameter | Remark |
|---|---|
| Three cycles Freeze (−20° C., 24 h) Thaw (25° C., 24 h) | Fails. Its unstable, even at RT |
| Stability at 45° C., over one month | Unstable, separates into two layers |
| Foam (5% in water. Hart DeGeorge) | 560 mL |

Example 1D: Comparative Example

Cleansing Oil Composition Using TIPA-Lauroyl Sarcosinate and Safflower Oil

| Ingredients | % (w/w) |
|---|---|
| Safflower Oil (*Carthamus tinctorius*) | 50 |
| Polyglyceryl-3 Oleate | 30 |
| Glyceryl Laurate | 5 |
| TIPA-Lauroyl Sarcosinate | 12 |
| Water | 3 |
| Total | 100 |

| Evaluation Parameter | Remark |
|---|---|
| Three cycles Freeze (−20° C., 24 h) Thaw (25° C., 24 h) | Passes |
| Stability at 45° C., over one month | Transparent but unstable in terms of color Color: 6.2 Gardner (Initial color: 1.2 Gardner) |
| Foam (5% in water. Hart DeGeorge) | 260 mL |

Example 1E: Comparative Example

Cleansing oil composition using TIPA-lauroyl sarcosinate and safflower oil

| Ingredients | % (w/w) |
|---|---|
| Sunflower Oil (*Helianthus annuus*) | 75 |
| Polyglyceryl-3 Oleate | 15 |
| TIPA-Lauroyl Sarcosinate | 10 |
| Total | 100 |

| Evaluation Parameter | Remark |
|---|---|
| Three cycles Freeze (−20° C., 24 h) Thaw (25° C., 24 h) | Unstable. Forms two layers |
| Stability at 45° C., over one month | Unstable. Forms two layers with increase in color from pale yellow to brown |
| Foam (5% in water. Hart DeGeorge) | 130 mL |

Example 2

Cleansing Oil Composition with Potassium N-Lauroyl L-Prolinate and Lauryl Lactylate

| Ingredients | % (w/w) |
|---|---|
| Safflower Oil (*Carthamus tinctorius*) | 50 |
| Polyglyceryl-3 Oleate | 30 |
| Lauryl Lactylate | 5 |
| Potassium N-Lauroyl L-Prolinate | 12 |
| Water | 3 |
| Total | 100 |

| Evaluation Parameter | Remark |
|---|---|
| Three cycles Freeze (−20° C., 24 h) Thaw (25° C., 24 h) | Passes |
| Stability at 45° C., over one month | Stable, Transparent Color: 190APHA (Initial color: 102 APHA) |
| Foam (5% in water. Hart DeGeorge) | 420 mL |

Example 3

Cleansing Oil Composition with Potassium N-Cocoyl L-Prolinate and Lauryl Lactate

| Ingredients | % (w/w) |
|---|---|
| Safflower Oil (*Carthamus tinctorius*) | 50 |
| Polyglyceryl-3 Oleate | 30 |
| Lauryl Lactate | 5 |
| Potassium N-Cocoyl L-Prolinate | 12 |
| Water | 3 |
| Total | 100 |

| Evaluation Parameter | Remark |
|---|---|
| Three cycles Freeze (−20° C., 24 h) Thaw (25° C., 24 h) | Passes |
| Stability at 45° C., over one month | Stable, Transparent Color: 207 APHA (Initial color: 113 APHA) |
| Foam (5% in water. Hart DeGeorge) | 440 mL |

Example 4

Cleansing Oil Composition with Potassium N-Cocoyl L-Prolinate and Lauryl Citrate

| Ingredients | % (w/w) |
|---|---|
| Safflower Oil (*Carthamus tinctorius*) | 50 |
| Polyglyceryl-3 Oleate | 30 |
| Lauryl Citrate | 5 |
| Potassium N-Cocoyl L-Prolinate | 12 |
| Water | 3 |
| Total | 100 |

| Evaluation Parameter | Remark |
|---|---|
| Three cycles Freeze (−20° C., 24 h) Thaw (25° C., 24 h) | Passes |
| Stability at 45° C., over one month | Stable, Transparent Color: 198 APHA (Initial color: 107 APHA) |
| Foam (5% in water. Hart DeGeorge) | 415 mL |

Example 5

Cleansing Oil Composition with Actives (Antiacne and Vitamins)

| Ingredients | % (w/w) |
|---|---|
| Sunflower Oil (*Helianthus annuus*) | 24 |
| Olive Oil (*Olea europaea*) | 21 |
| Polyglyceryl-3 Oleate | 30 |
| Glyceryl Laurate | 5 |
| Potassium N-Lauroyl L-Prolinate | 15 |
| Water | 2.5 |
| Niacinamide | 0.5 |
| Undecylenoyl Glycine | 0.5 |
| Vitamin E | 0.5 |
| DL-Panthenol | 0.5 |
| Fragrance | 0.5 |
| Total | 100 |

| Evaluation Parameter | Remark |
|---|---|
| Three cycles Freeze (−20° C., 24 h) Thaw (25° C., 24 h) | Passes |
| Stability at 45° C., over one month | Stable, Transparent Color: 255 APHA (Initial color: 148 APHA) |
| Foam (5% in water. Hart DeGeorge) | 470 mL |

Example 6

Cleansing Oil Composition with Combination of Oils

| Ingredients | % (w/w) |
|---|---|
| Soybean Oil (*Glycine soja*) | 40 |
| Sunflower Seed Oil | 8.5 |
| Polyglyceryl-3 Oleate | 30 |
| Alpha-eleostearic acid | 2.5 |
| Cinnamon Oil | 2.5 |
| Potassium N-Lauroyl L-Prolinate | 15 |
| Water | 0.5 |
| Capryloyl Glycine | 0.5 |
| Vitamin E | 0.5 |
| Total | 100 |

| Evaluation Parameter | Remark |
|---|---|
| Three cycles Freeze (−20° C., 24 h) Thaw (25° C., 24 h) | Passes |
| Stability at 45° C., over one month | Stable, Transparent Color: 270 APHA (Initial color: 135 APHA) |
| Foam (5% in water. Hart DeGeorge) | 455 mL |

Example 7

Cleansing Oil Composition with Olive Oil and Potassium N-Cocoyl L-Prolinate

| Ingredients | % (w/w) |
| --- | --- |
| Olive Oil (*Olea europaea*) | 35 |
| Palm Kernel Oil (*Elaeis guineensis*) | 5 |
| Polyglyceryl-3 Oleate | 35 |
| Potassium N-Cocoyl L-Prolinate | 20 |
| Water | 3 |
| Capryloyl Glycine | 0.5 |
| Undecylenoyl Glycine | 0.5 |
| DL-Panthenol | 0.5 |
| Fragrance | 0.5 |
| Total | 100 |

| Evaluation Parameter | Remark |
| --- | --- |
| Three cycles Freeze (−20° C., 24 h) Thaw (25° C., 24 h) | Passes |
| Stability at 45° C., over one month | Stable, Transparent Color: 228 APHA (Initial color: 135 APHA) |
| Foam (5% in water. Hart DeGeorge) | 520 mL |

Example 8

Cleansing Oil Composition with Avocado Oil and Shae Butter

| Ingredients | % (w/w) |
| --- | --- |
| Sunflower Seed Oil (*Helianthus annuus*) | 30 |
| Avocado Oil | 8 |
| Shea Butter (*Butyrospermum parkii*) | 4 |
| Coconut Oil | 4 |
| Polyglyceryl-3 Oleate | 30 |
| Glyceryl Laurate | 3 |
| Coco Glycerides | 2 |
| Potassium N-Cocoyl L-Prolinate | 15 |
| Water | 2 |
| Capryloyl Glycine | 0.5 |
| Undecylenoyl Glycine | 0.5 |
| Vitamin E | 0.5 |
| Fragrance | 0.5 |
| Total | 100 |

| Evaluation Parameter | Remark |
| --- | --- |
| Three cycles Freeze (−20° C., 24 h) Thaw (25° C., 24 h) | Passes |
| Stability at 45° C., over one month | Stable, Transparent Color: 198 APHA (Initial color: 98 APHA) |
| Foam (5% in water. Hart DeGeorge) | 480 mL |

Example 9

Cleansing Oil Composition with Skin Care Additives

| Ingredients | % (w/w) |
| --- | --- |
| Soybean Oil | 35 |
| Jojoba Oil | 8 |
| Polyglyceryl-3 Oleate | 30 |
| Glyceryl Laurate | 5 |
| Potassium N-Cocoyl L-Prolinate | 15 |
| Water | 3 |
| DL-Panthenol | 1.5 |
| Undecylenoyl Glycine | 0.5 |
| Ascorbic Acid | 1.0 |
| Ceraminde-3 | 0.5 |
| Fragrance | 0.5 |
| Total | 100 |

| Evaluation Parameter | Remark |
| --- | --- |
| Three cycles Freeze (−20° C., 24 h) Thaw (25° C., 24 h) | Passes |
| Stability at 45° C., over one month | Stable, Transparent Color: 208 APHA (Initial color: 114 APHA) |
| Foam (5% in water. Hart DeGeorge) | 465 mL |

Example 10

Cleansing Oil Composition with Jojoba Oil and Neem Oil

| Ingredients | % (w/w) |
| --- | --- |
| Soybean Oil (*Glycine soja*) | 45 |
| Jojoba Oil (*Simmondsia chinensis*) | 2 |
| Neem Oil (*Azadirachta indica* seed oil) | 2 |
| Polyglyceryl-3 Oleate | 30 |
| Caprylic Capric Triglyceride | 4 |
| Potassium N-Lauroyl L-Prolinate | 15 |
| Ascorbic Acid | 0.5 |
| Water | 1 |
| Fragrance | 0.5 |
| Total | 100 |

| Evaluation Parameter | Remark |
| --- | --- |
| Three cycles Freeze (−20° C., 24 h) Thaw (25° C., 24 h) | Passes |
| Stability at 45° C., over one month | Stable, Transparent Color: 278 APHA (Initial color: 158 APHA) |
| Foam (5% in water. Hart DeGeorge) | 460 mL |

Example 11

Cleansing Oil Composition with Almond Oil

| Ingredients | % (w/w) |
| --- | --- |
| Sunflower Seed Oil | 48 |
| Almond Oil | 8 |
| Polyglyceryl-3 Oleate | 24 |

-continued

| Ingredients | % (w/w) |
|---|---|
| Glyceryl Laurate | 4 |
| Potassium N-Lauroyl L-Prolinate | 12 |
| Water | 1 |
| DL-Panthenol | 1 |
| Vitamin E | 1.5 |
| Fragrance | 0.5 |
| Total | 100 |

| Evaluation Parameter | Remark |
|---|---|
| Three cycles Freeze (−20° C., 24 h) Thaw (25° C., 24 h) | Passes |
| Stability at 45° C., over one month | Stable, Transparent Color: 202 APHA (Initial color: 95 APHA) |
| Foam (5% in water. Hart DeGeorge) | 455 mL |

Example 12

Cleansing Oil Composition with Neem Oil and Tung Seed Oil

| Ingredients | % (w/w) |
|---|---|
| Sunflower Seed Oil (*Helianthus annuus*) | 35 |
| Citronella Oil (*Cymbopogon nardus*) | 2 |
| Cedarwood Oil (*Cedrus deodard*) | 2 |
| Neem Seed Oil | 2 |
| Lavender Oil | 2 |
| Tung Oil (*Aleurites fordil*) | 2 |
| Polyglyceryl-3 Oleate | 30 |
| Glyceryl Laurate | 4 |
| Potassium N-Lauroyl L-Prolinate | 15 |
| Water | 3 |
| DL-Panthenol | 1 |
| Vitamin E | 2 |
| Total | 100 |

| Evaluation Parameter | Remark |
|---|---|
| Three cycles Freeze (−20° C., 24 h) Thaw (25° C., 24 h) | Passes |
| Stability at 45° C., over one month | Stable, Transparent Color: 304 APHA (Initial color: 152 APHA) |
| Foam (5% in water. Hart DeGeorge) | 470 mL |

Example 13

| Cleansing oil composition with coconut and argan oil | |
|---|---|
| Ingredients | % (w/w) |
| Coconut Oil (*Cocos nucifera*) | 35 |
| Argan Oil (*Argnia spinosa*) | 5 |
| Rapeseed Oil (*Brassica napus* subsp. *Napus*) | 5 |
| Polyglyceryl-3 Oleate | 30 |
| Potassium N-Lauroyl L-Prolinate | 12 |
| DL-Panthenol | 1 |
| L-Arginine | 0.5 |

-continued

| Cleansing oil composition with coconut and argan oil | |
|---|---|
| Ingredients | % (w/w) |
| Glyceryl Laurate | 6 |
| Indian Gooseberry extract (*Phyllanthus emblica*) | 0.1 |
| Water | 2.4 |
| Vitamin E | 2 |
| Undecylenoyl Glycine | 0.5 |
| Capryloyl Glycine | 0.5 |
| Total | 100 |

| Evaluation Parameter | Remark |
|---|---|
| Three cycles Freeze (−20° C., 24 h) Thaw (25° C., 24 h) | Passes |
| Stability at 45° C., over one month | Stable, Transparent Color: 194 APHA (Initial color: 87 APHA) |
| Foam (5% in water. Hart DeGeorge) | 465 mL |

Example 14

Cleansing Oil Composition with Coconut Oil

| Ingredients | % (w/w) |
|---|---|
| Coconut Oil (*Cocos Nucifera*) | 30 |
| Castor Oil (*Ricinus communis*) | 5 |
| Polyglyceryl-3 Oleate | 35 |
| Potassium N-Lauroyl L-Prolinate | 15 |
| DL-Panthenol | 1.5 |
| L-Arginine | 0.5 |
| Glyceryl Laurate | 7 |
| Water | 3 |
| Vitamin E | 2 |
| Undecylenoyl Glycine | 0.5 |
| Capryloyl Glycine | 0.5 |
| Total | 100 |

| Evaluation Parameter | Remark |
|---|---|
| Three cycles Freeze (−20° C., 24 h) Thaw (25° C., 24 h) | Passes |
| Stability at 45° C., over one month | Stable, Transparent Color: 210 APHA (Initial color: 92 APHA) |
| Foam (5% in water. Hart DeGeorge) | 480 mL |

Example 15

Cleansing Oil Composition with Potassium N-Coccoyl L-Prolinate, Glyceryl Laurate and Lauryl Lactate

| Ingredients | % (w/w) |
|---|---|
| Safflower Oil (*Carthamus tinctorius*) | 50 |
| Polyglyceryl-3 Oleate | 18 |
| Lauryl Lactate | 10 |

-continued

| Ingredients | % (w/w) |
|---|---|
| Glyceryl Laurate | 5.5 |
| Potassium N-Cocoyl L-Prolinate | 15 |
| Water | 1.5 |
| Total | 100 |

| Evaluation Parameter | Remark |
|---|---|
| Three cycles Freeze (−20° C., 24 h) Thaw (25° C., 24 h) | Passes |
| Stability at 45° C., over one month | Stable, Transparent Color: 210 APHA (Initial color: 118 APHA) |
| Foam (5% in water. Hart DeGeorge) | 420 mL |

Example 16

Cleansing Oil Composition with Potassium N-Coccoyl L-Prolinate and Glyceryl Laurate

| Ingredients | % (w/w) |
|---|---|
| Safflower Oil (*Carthamus tinctorius*) | 47.5 |
| Polyglyceryl-3 Oleate | 36 |
| Glyceryl Laurate | 4 |
| Potassium N-Cocoyl L-Prolinate | 12 |
| Water | 0.5 |
| Total | 100 |

| Evaluation Parameter | Remark |
|---|---|
| Three cycles Freeze (−20° C., 24 h) Thaw (25° C., 24 h) | Passes |
| Stability at 45° C., over one month | Stable, Transparent Color: 224 APHA (Initial color: 120 APHA) |
| Foam (5% in water. Hart DeGeorge) | 400 mL |

Example 17

Cleansing Oil Composition Using Potassium N-Lauroyl L-Prolinate and Safflower Oil

| Ingredients | % (w/w) |
|---|---|
| Sunflower Oil (*Helianthus annuus*) | 75 |
| Polyglyceryl-3 Oleate | 15 |
| Potassium N-Lauroyl L-Prolinate | 10 |
| Total | 100 |

| Evaluation Parameter | Remark |
|---|---|
| Three cycles Freeze (−20° C., 24 h) Thaw (25° C., 24 h) | Passes |
| Stability at 45° C., over one month | Stable, Transparent Color: 262 APHA (Initial color: 130 APHA) |
| Foam (5% in water. Hart DeGeorge) | 320 mL |

We claim:
1. A transparent vegetable oil-based cleansing composition comprising:
 (a) Potassium N-Acyl L-Prolinate of Formula I,

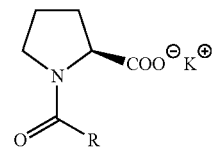

Formula I wherein R is selected from cocoyl and lauroyl;
 (b) Polyglyceryl-3 Oleate of Formula II;

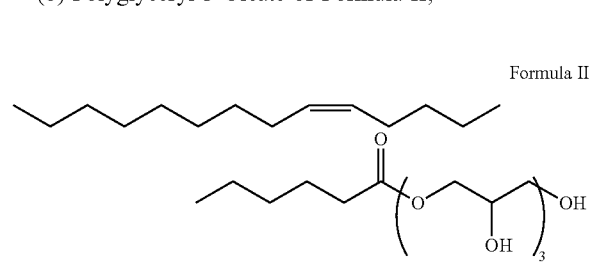

Formula II (c) one or more vegetable oils;
(d) optionally, emollients, skin and hair care actives; and
(e) 0% to 3% of water by weight of the cleansing composition,
 wherein the transparent vegetable oil-based cleansing composition is stable after three freeze-thaw cycles, each cycle involving 24 h of freezing at −20° C. and followed by thawing to 25° C. for 24 h.

2. The transparent vegetable oil-based cleansing composition as claimed in claim 1, wherein the one or more vegetable oils is selected from safflower oil, soybean oil, sunflower oil, coconut oil, palm kernel oil, olive oil, jojoba oil, neem oil, macadamia oil, argan oil, almond oil, avocado oil, grapeseed oil, soap nut oil, meadowfoam seed oil, wheat germ oil, rice bran oil, rosemary oil, castor oil, rapeseed oil, tung oil, mustard oil, peanut oil and shea butter.

3. The transparent vegetable oil-based cleansing composition as claimed in claim 2, wherein the one or more vegetable oils is selected from safflower oil, sunflower oil, soybean oil, castor oil, olive oil, and mixtures thereof.

4. The transparent vegetable oil-based cleansing composition as claimed in claim 1, wherein the skin and hair care actives are selected from vitamin E, vitamin D, niacinamide, ceramides, panthenol, essential oils, lavender oil, citronella oil, neem oil, tea tree oil, emollient esters derived from bio-renewable source, caprylic capric triglyceride, glyceryl mono laurate, glyceryl mono oleate, glyceryl mono cocoate, and polyglyceryl esters of fatty acids.

5. The transparent vegetable oil-based cleansing composition as claimed in claim 1, wherein a ratio of Potassium N-Acyl L-Prolinate:Polyglyceryl-3 Oleate: one or more vegetable oil is 1.5:2.0 to 4.5:3.0 to 7.5.

* * * * *